(12) United States Patent
Hsiao

(10) Patent No.: US 8,983,277 B2
(45) Date of Patent: Mar. 17, 2015

(54) ANGLE-ADJUSTABLE AROMA DIFFUSER

(71) Applicant: Ming Jen Hsiao, Miaoli County (TW)

(72) Inventor: Ming Jen Hsiao, Miaoli County (TW)

( * ) Notice: Subject to any disclaimer, the term of this patent is extended or adjusted under 35 U.S.C. 154(b) by 0 days.

(21) Appl. No.: 14/157,284

(22) Filed: Jan. 16, 2014

(65) Prior Publication Data

US 2014/0133841 A1     May 15, 2014

Related U.S. Application Data

(63) Continuation-in-part of application No. 13/669,411, filed on Nov. 5, 2012, now Pat. No. 8,787,739, and a continuation-in-part of application No. 13/669,402, filed on Nov. 5, 2012, and a continuation-in-part of application No. 13/870,829, filed on Apr. 25, 2013.

(51) Int. Cl.
| | |
|---|---|
| *A61M 16/00* | (2006.01) |
| *F24F 3/14* | (2006.01) |
| *A61L 9/16* | (2006.01) |

(52) U.S. Cl.
CPC .................................... *A61L 9/16* (2013.01)
USPC .......................................... 392/390; 392/386

(58) Field of Classification Search
None
See application file for complete search history.

(56) References Cited

U.S. PATENT DOCUMENTS

| | | | | |
|---|---|---|---|---|
| 949,606 | A * | 2/1910 | Tetherow | 219/429 |
| 1,431,719 | A * | 10/1922 | Brown | 392/403 |
| 1,547,160 | A * | 7/1925 | Bailey | 219/473 |
| 2,043,647 | A * | 6/1936 | Berven | 261/136 |
| 2,742,342 | A * | 4/1956 | Dew et al. | 422/37 |
| 2,881,303 | A * | 4/1959 | Resk | 392/403 |
| 3,587,968 | A | 6/1971 | Hennart et al. | |
| 3,959,642 | A * | 5/1976 | Turro | 362/92 |
| 4,544,592 | A * | 10/1985 | Spector | 428/68 |
| 4,647,433 | A * | 3/1987 | Spector | 422/125 |
| 4,781,895 | A * | 11/1988 | Spector | 422/125 |
| 5,647,052 | A * | 7/1997 | Patel et al. | 392/390 |
| 5,651,942 | A * | 7/1997 | Christensen | 422/125 |
| 5,796,914 | A * | 8/1998 | Gatzemeyer et al. | 392/390 |
| 6,031,967 | A * | 2/2000 | Flashinski et al. | 392/390 |
| 6,085,026 | A * | 7/2000 | Hammons et al. | 392/390 |
| 6,349,168 | B1 * | 2/2002 | Jaworski | 392/392 |
| 6,435,563 | B2 | 8/2002 | Phillips | |
| 6,663,838 | B1 * | 12/2003 | Soller et al. | 422/125 |
| 6,772,756 | B2 * | 8/2004 | Shayan | 128/203.26 |

(Continued)

FOREIGN PATENT DOCUMENTS

| | | |
|---|---|---|
| AU | 2012101327 | 1/2013 |
| EP | 0321729 | 6/1989 |

(Continued)

*Primary Examiner* — Thor Campbell
(74) *Attorney, Agent, or Firm* — Ming Chow; Sinorica, LLC

(57) ABSTRACT

An angle-adjustable aroma diffuser is provided, including a hollow housing, a heat-transfer container, a heating component and an angle-adjustable electric plug. The hollow housing has a first opening and a second opening. The heat-transfer container is mounted in the hollow housing. The heating component is combined with a bottom side of the heat-transfer container. The angle-adjustable electric plug is combined with the second opening of the hollow housing. The angle-adjustable electric plug is electrically connected to the heating component. Therefore, an aroma capsule can be disposed in the heat-transfer container through the open end, the hollow housing and the heat-transfer container of the angle-adjustable aroma diffuser can rotate upward and modulate an angle, and the aroma capsule generates fragrance upward through the open end of the heat-transfer container.

9 Claims, 9 Drawing Sheets

(56) References Cited

U.S. PATENT DOCUMENTS

| | | | |
|---|---|---|---|
| 7,046,919 B2 * | 5/2006 | Shimizu et al. | 392/390 |
| 7,095,953 B2 * | 8/2006 | Caserta et al. | 392/390 |
| 7,572,412 B2 * | 8/2009 | Yang | 422/124 |
| D604,699 S | 11/2009 | Yamamoto | |
| 7,670,566 B2 * | 3/2010 | Adair et al. | 422/125 |
| 8,047,837 B2 * | 11/2011 | Furner et al. | 431/291 |
| 8,068,725 B2 | 11/2011 | Cheung | |
| 8,262,277 B2 * | 9/2012 | Hsiao | 362/643 |
| 8,265,465 B2 | 9/2012 | Jorgensen | |
| 8,265,466 B2 * | 9/2012 | Jorgensen | 392/393 |
| 8,281,514 B2 * | 10/2012 | Fleming | 43/129 |
| D692,548 S | 10/2013 | Wirz | |
| D692,550 S | 10/2013 | Wirz | |
| 8,716,632 B1 * | 5/2014 | Pesu et al. | 219/438 |
| 8,750,694 B1 * | 6/2014 | Porretta et al. | 392/395 |
| 2002/0176704 A1 * | 11/2002 | Roe | 392/393 |
| 2005/0016985 A1 * | 1/2005 | Haas et al. | 219/438 |
| 2005/0274818 A1 * | 12/2005 | Ghazarian | 239/34 |
| 2007/0014549 A1 * | 1/2007 | Demarest et al. | 392/393 |
| 2007/0047931 A1 * | 3/2007 | Niemeyer | 392/390 |
| 2008/0013932 A1 * | 1/2008 | He et al. | 392/390 |

FOREIGN PATENT DOCUMENTS

| | | |
|---|---|---|
| EP | 1473046 | 11/2004 |
| EP | 1627647 | 2/2006 |
| EP | 2067491 | 6/2009 |
| JP | 2002369705 | 12/2002 |

* cited by examiner

US 8,983,277 B2

ANGLE-ADJUSTABLE AROMA DIFFUSER

CROSS-REFERENCE TO RELATED ART

The present invention is a continuation-in-part of U.S. patent application Ser. No. 13/669,402 filed on Nov. 5, 2012, Ser. No. 13/669,411 filed on Nov. 5, 2012 and Ser. No. 13/870,829 filed on Apr. 25, 2013.

BACKGROUND OF THE INVENTION

1. Field of the Invention

This invention relates to aroma diffusers, and, more particularly, to an angle-adjustable aroma diffuser.

2. Description of Related Art

Many aroma diffusing devices are known and commercially available. Exemplars are seen in U.S. Pat. No. 8,066,420 entitled "Aroma diffusing night lamp system having an angle-adjustable electric plug (5)", U.S. Pat. No. 8,262,277A entitled "Aroma diffusing night lamp system with an angle-adjustable electric plug (5)", and U.S. Pat. No. 8,147,116 entitled "Safety lamp bulb connector assembly". These aroma diffusing devices commonly include a power source, a lamp, and a container for holding an essential oil or aromatic substance. Dumping of these aroma diffusing devices can be prone to danger. Further, after each use, the user needs to remove essential oil or aromatic substance residues from the container, and then to clean or wash the device, and then to put a new amount of essential oil or aromatic substance in the container, complicating the essential oil or aromatic substance supplying operation.

Further, most conventional aroma diffusing devices do not allow change of the diffusing direction or electric plug installation angle to fit different application requirements, different application places or different electric socket positions. Further, conventional aroma diffusing devices are commonly designed for use in particular places. For example, an aroma diffusing device designed for home or office use may be not suitable for use in a car. Further, the prior art aroma diffusing devices that allow change of the diffusing angle have the drawbacks of complicated structure, high manufacturing cost and high failure rate.

Therefore, it is desirable to provide an aroma diffuser that eliminates the aforesaid problems.

SUMMARY OF THE INVENTION

In view of the above-mentioned problems of the prior art, it is an objective of the present invention to provide an angle-adjustable aroma diffuser that has an adjustable angle, and is easy and safe to use. An aroma diffuser in accordance with the present invention can be combined with a disposable aroma capsule, in which the aromatic substance will not flow to a region outside of the aroma diffuser even if the aroma diffuser is toppled and fell on the ground. The aroma capsule can be disposed after the aromatic substance is volatile completely. It is also convenient to change a new aroma capsule.

In an embodiment, the angle-adjustable aroma diffuser comprises a hollow housing; a heat-transfer container; a heating component; and an angle-adjustable electric plug, wherein the hollow housing comprises a first opening and a second opening, the heat-transfer container is mounted in the hollow housing, the heat-transfer container has an open end facing toward the same direction as the first opening, the heating component is combined to a bottom side of the heat-transfer container, the angle-adjustable electric plug has one side combined with the second opening of the hollow housing, and the angle-adjustable electric plug is electrically connected to the heating component.

The angle-adjustable electric plug further comprises a pivot cover and a hollow pivot body.

The angle-adjustable electric plug comprises an axle, a ratchet disposed on one side of the axle, and an electric outlet disposed on the other side of the axle, the axle is disposed on an inner side of the ratchet, the pivot cover comprises an axle groove, the hollow pivot body comprises a damping block and a magazine, the damping block is formed on an inner side of the hollow pivot body, the magazine is disposed on one side of the hollow pivot body, the pivot cover is combined with one side of the hollow pivot body, the axle of the angle-adjustable electric plug passes through the axle groove, the ratchet props against the damping block, the angle-adjustable electric plug changes an angle through the axle in the magazine, the electric outlet is combined with a socket, the hollow housing of the angle-adjustable aroma diffuser and the heat-transfer container modulate an angle upward with respect to the angle-adjustable electric plug through the use of the ratchet and a damping function of the damping block.

The heat-transfer container further comprises a screw bracket disposed on the bottom side of the heat-transfer plate and a screw, the screw bracket comprises a screw hole, the heating component props against a bottom portion of the heat-transfer plate, the heating component has a bottom side combined with a cushion pad, the heating component and the cushion pad are disposed on an inner side of the screw bracket, the screw passes through the screw hole and props against the cushion pad to push the heating component upward such that the heating component is in close contact with the heat-transfer plate disposed on a bottom portion of the heat-transfer container.

The heat-transfer container is an insulating material that does not conduct heat, the heat-transfer plate is metal, and the heating component generates heat that is transferred to the heat-transfer plate to heat the aroma capsule, without diffused to a region outside of the hollow housing.

The angle-adjustable aroma diffuser further comprises a PCB disposed in the hollow housing, the PCB is electrically connected to the angle-adjustable electric plug and the heating component, the PCB comprises another screw hole, the another screw has one end passing through the screw hole, the another screw has one end screwed to the hollow housing and the other end combined with the screw bracket, a heat-proof hollow pillar is combined with one end of the another screw and in contact with the screw bracket on the bottom side of the heat-transfer plate, for isolating the heat generated by the heating component from being transferred to the PCB.

The aroma diffuser further comprises a light-guiding ring and a light-emitting device, the light-emitting device is disposed in the aroma diffuser near one side of the light-guiding ring, and the light-emitting device is electrically connected to the electric outlet.

The cushion pad is L-shaped, and the L-shaped cushion pad props against the heating component in the screw bracket.

The heat-transfer container further comprises a magazine disposed on a top periphery thereof, the magazine comprises a slope portion and a groove portion extending from the slope portion, the groove portion has a concave portion disposed on a top side thereof, the angle-adjustable aroma diffuser further comprises a cover that has a through hole and a protrusion, and the cover is hooked in the concave portion of the magazine of the heat-transfer container by using the protrusion.

An aroma capsule disposed in the heat-transfer container, the aroma capsule further comprises a disposable capsule body and an aromatic substance, the disposable capsule body has a top opening, the aromatic substance is disposed in the disposable capsule body, and the aroma capsule further comprises a breathing film that is combined with the top opening of the disposable capsule body.

The present invention has the following advantages. The angle-adjustable electric plug can be combined with a power unit. The hollow housing, the first opening, the heat-transfer container and the open end of the angle-adjustable aroma diffuser can rotate upward and modulate an angle with respect to the angle-adjustable electric plug, allowing the heat-transfer container and the open end to face upward. An aroma capsule can be disposed in the heat-transfer container through the open end. The power unit supplies power to the heating component and enables the heating component to generate heat. The heat will be transferred to the heat-transfer container and heat upward, for the aromatic substance to generate fragrance. The angle-adjustable aroma diffuser in accordance with the present invention can be used in a power socket in a car. The hollow housing can rotate with respect to the angle-adjustable electric plug. The open end of the heat-transfer container and the aroma capsule contained therein face upward at a certain angle. Therefore, even if the aroma capsule is toppled or fell to the ground, the aromatic substance will be blocked by the breathing film from flowing out. Therefore, the aromatic substance will not contaminate the environment or the dashboard.

BRIEF DESCRIPTION OF DRAWINGS

The invention can be more fully understood by reading the following detailed description of the preferred embodiments, with reference made to the accompanying drawings, wherein.

DETAILED DESCRIPTION OF THE INVENTION

Figure 1:
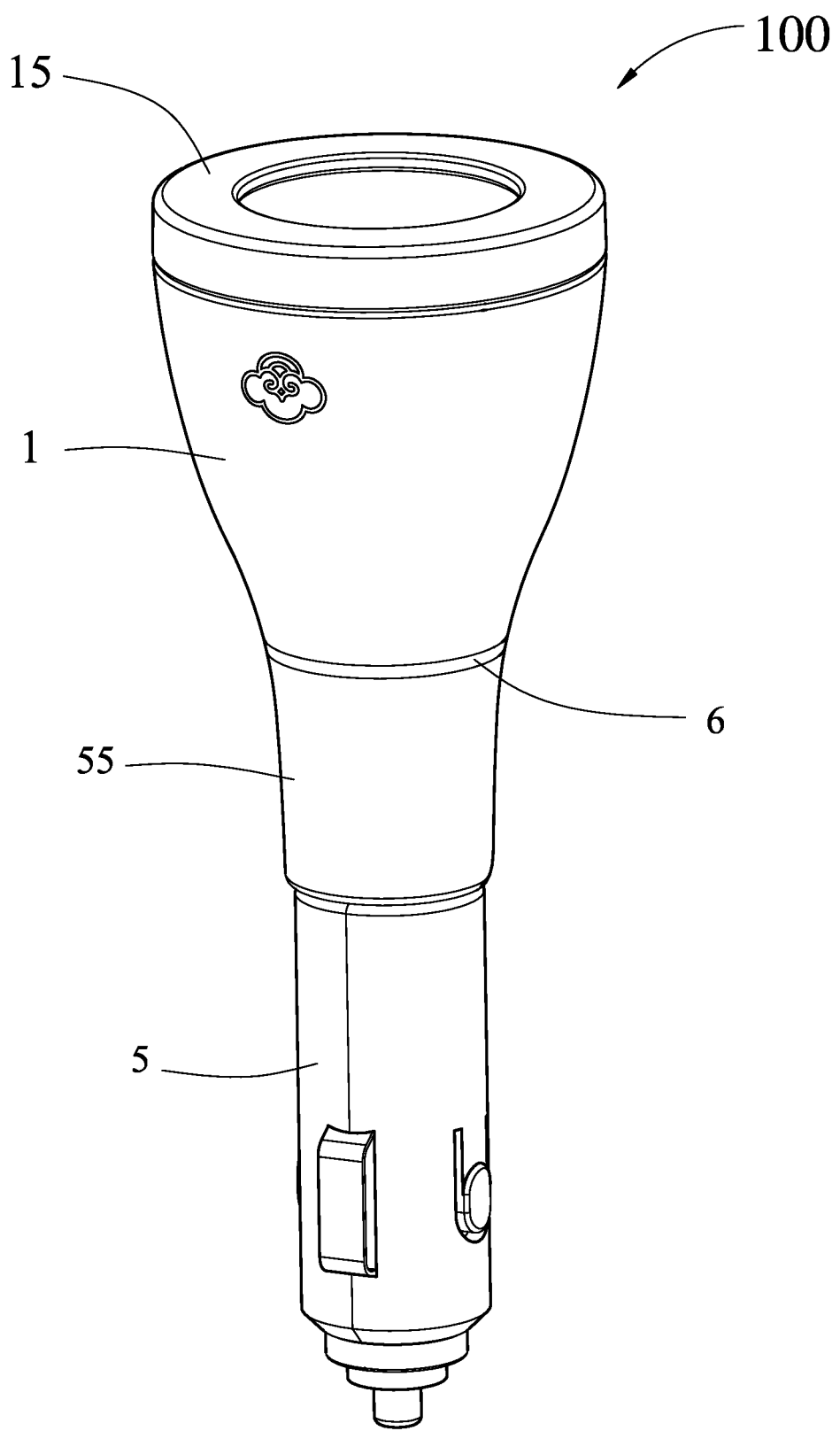
FIG. 1 is an elevational view of an angle-adjustable aroma diffuser in accordance with the present invention.
Figure 2:
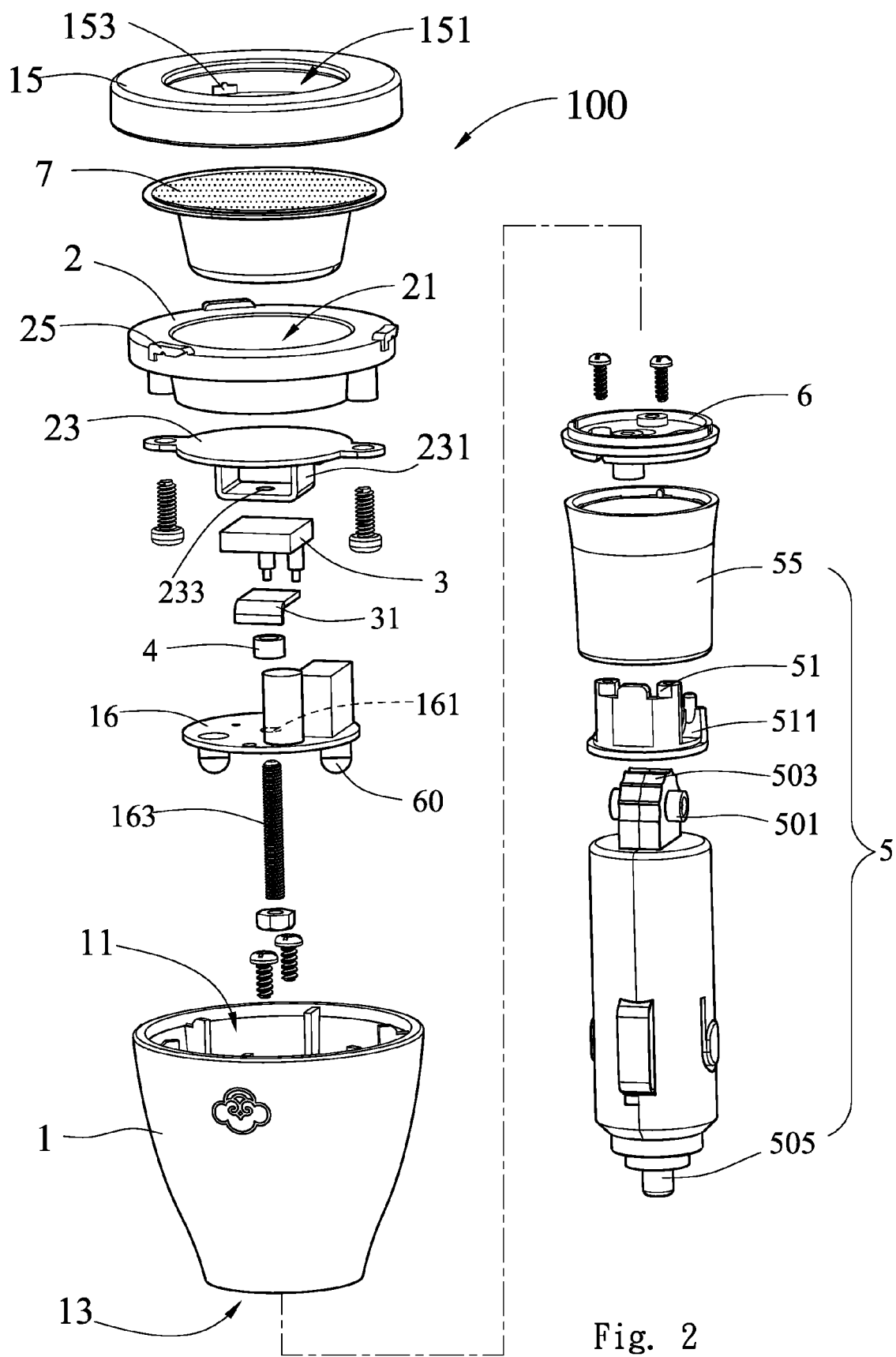
FIG. 2 is an exploded view of the angle-adjustable aroma diffuser in accordance with the present invention.
Figure 3:
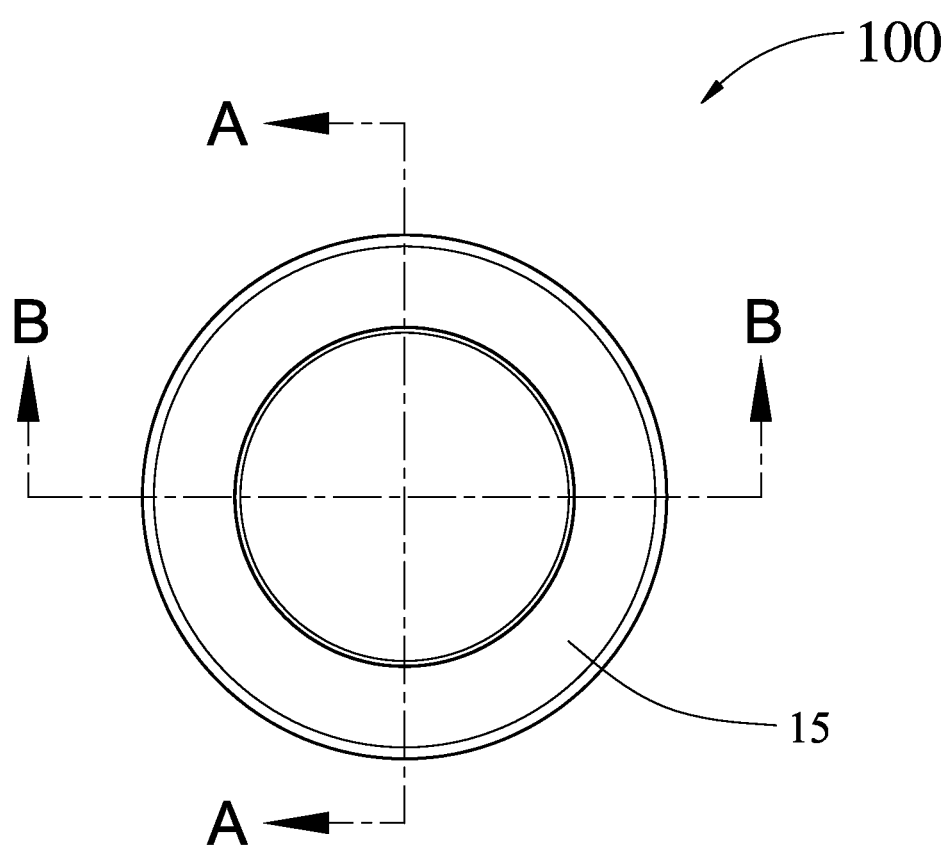
FIG. 3 is a top view of the angle-adjustable aroma diffuser in accordance with the present invention.

In the following detailed description, for purposes of explanation, numerous specific details are set forth in order to provide a through understanding of the disclosed embodiments. It will be apparent, however, that one or more embodiments may be practiced without these specific details. In other instances, well-known structures and devices are schematically shown in order to simplify the drawing.

Refer to FIGS. 1-4, which show an embodiment in accordance with the present invention. An angle-adjustable aroma diffuser 100 comprises a hollow housing 1, a heat-transfer container 2, a heating device 3, and an angle-adjustable electric plug 5. The hollow housing 1 has a first opening 11 and a second opening 13. The heat-transfer container 2 is mounted in the hollow housing 1, and has an open end 21 facing toward the first opening 11. The heating device 3 is mounted to a bottom side of the heat-transfer container 2. The angle-adjustable electric plug 5 is electrically connected to the heating component 3. The angle-adjustable electric plug 5 is connected to the second opening 13 of the hollow housing 1. Therefore, the hollow housing 1 can rotate with respect with the angle-adjustable electric plug 5, and the hollow housing 1 and the angle-adjustable electric plug 5 have an included angle that is adjustable. The angle-adjustable electric plug 5 can be mounted to a power unit (not shown). The hollow housing 1, the first opening 11, the heat-transfer container 2, and the open end 21 of the angle-adjustable aroma diffuser 100 can rotate to face upward and have an angle adjustable, allowing the heat-transfer container 2 and the open end 21 to face upward, while the heat-transfer container 2 of the angle-adjustable aroma diffuser 100 can be adjusted by an angle from a vertical direction and occupy less capacity.

The angle-adjustable aroma diffuser 100 can be used in a power socket in a car. The first opening 11 of the hollow housing 1 and the open end 21 of the heat-transfer container 2 of the angle-adjustable aroma diffuser 100 can have an angle adjusted and rotate upward with respect to the angle-adjustable electric plug 5, allowing the heat-transfer container 2 and the open end 21 to face upward. An aroma capsule 7 can be placed in the heat-transfer container 2 through the open end 21. A power unit (not shown) supplies power to the heating component 3, and the heating component 3 generates heat, which is transferred upward by the heat-transfer container 2 to enable the aroma capsule 7 to generate aroma.

Please refer to FIGS. 1 and 7-9 at the same time. The angle-adjustable electric plug 5 comprises an axle 501, a ratchet 503 disposed on one side of the axle 501, and an electric outlet 505 disposed on the other side of the axle 501. The axle 501 is disposed on an inner side of the ratchet 503. The pivot cover 51 comprises an axle groove 511. The hollow pivot body 55 comprises a damping block 551 and a magazine 553. The damping block 551 is disposed on an inner side of the hollow pivot body 55. The magazine 553 is disposed on one side of the hollow pivot body 55. The pivot cover 51 is mounted to an inner side of the hollow pivot body 55. The axle 501 of the angle-adjustable electric plug 5 is installed in the axle groove 511 by passing itself therethrough. The ratchet 503 props against the damping block 551. Therefore, one side of the angle-adjustable electric plug 5, when passing the axle in the magazine 553, rotates and changes its angle. The electric outlet 505 is mounted to a socket. The hollow housing 1 and the heat-transfer container 2 of the angle-adjustable aroma diffuser 100 can modulate an angle upward with respect the angle-adjustable electric plug 5, through the use of the ratchet 503 and the damping effect of the damping block 551, allowing the first opening 11 of the hollow housing 1 and the open end 21 of the heat-transfer container 2 to be fixed upward. The aroma capsule 7 disposed in the heat-transfer container 2 is heated and diffuses aroma upward through the open end 21. The angle-adjustable electric plug 5 is horizontally or vertically disposed by the ratchet 503, and will be hooked by the magazine 553 when disposed with respect to the hollow housing 1 at a greatest usage angle, thus preventing the aroma capsule disposed in the heat-transfer container 2 from being heated downward.

The heat-transfer container 2 comprises a heat-transfer plate 23 on a bottom portion thereof. The heat-transfer plate 23 is mounted to or disposed on a bottom side of the heat-transfer container 2.

The heat-transfer container 2 further comprises a screw bracket 231 disposed on a bottom side of the heat-transfer plate 23. The screw bracket 231 comprises a screw hole 233. The heating device 3 props against the heat-transfer plate 23 at a bottom thereof. The heating device 3 has a bottom side that is mounted to a cushion pad 31. Both the heating device 3 and the cushion pad 31 are disposed on an inner side of the screw bracket 231. The screw 163 just passes the screw hole 233, and props against the cushion pad 31 and pushes the heating component 3 upward. Therefore, the heating component 3 is in close contact with the bottom surface the heat-transfer plate 23 under the heat-transfer container 2, and the heating component 3 does not move with respect to the heat-transfer plate 23.

The heat-transfer container 2 is made of an insulating material that does not conduct heat. The heat-transfer plate 23 is made of metal. The heating device 3 generates heat that is conducted to the heat-transfer plate 23 and heats the aroma capsule 7. Since the peripheral housing of the heat-transfer container 2 does not conduct heat, the outer portion of the present invention does not conduct heat and will not be heated up.

The angle-adjustable aroma diffuser 100 further comprises a PCB 16 mounted in the hollow housing 1. The PCB 16 is electrically connected to the angle-adjustable electric plug 5 and the heating component 3. The PCB 16 has a screw hole 161. The screw 163 has one side passing through the screw hole 161. The screw 163 has one end screwed and fixed to the hollow housing 1. The screw 163 has the other end mounted to the screw bracket 231. A heat-proof hollow pillar 4 is mounted to one end of the screw 163 and in contact with the screw bracket 231 on the bottom side of the heat-transfer plate 23, for isolating the heat generated by the heating component 3 from being conducted to the PCB 16, to ensure that the PCB 16 can function normally.

Please refer to FIGS. 2-5 at the same time. In an embodiment in accordance with the present invention, the aroma diffuser further comprises a light-guiding ring 6 and a light-emitting device 60. The light-guiding ring 6 is mounted between the second opening 13 of the hollow housing 1 and the hollow pivot body 55. The light-emitting device 60 is disposed in the aroma diffuser near one side of the light-guiding ring 6. In an embodiment, the light-emitting device 60 is disposed on one side of the PCB 16. The light-emitting device 60 is electrically connected to the electric outlet 515. When the light-emitting device 60 emits light and the light is projected onto the light-guiding ring 6, a soft halo effect is generated. The light-emitting device 60 can be used as a night lamp or remind a user that the aroma diffuser is in operation.

In an embodiment, the cushion pad 31 in L-shaped, and props against the heating device 3 to fix the heating device 3 to an inner side of the screw bracket 231. The heating component 3 is a resistor or another electrically heating element. In an embodiment, the heating device 3 is a PTC (thermistor).

Figure 6:
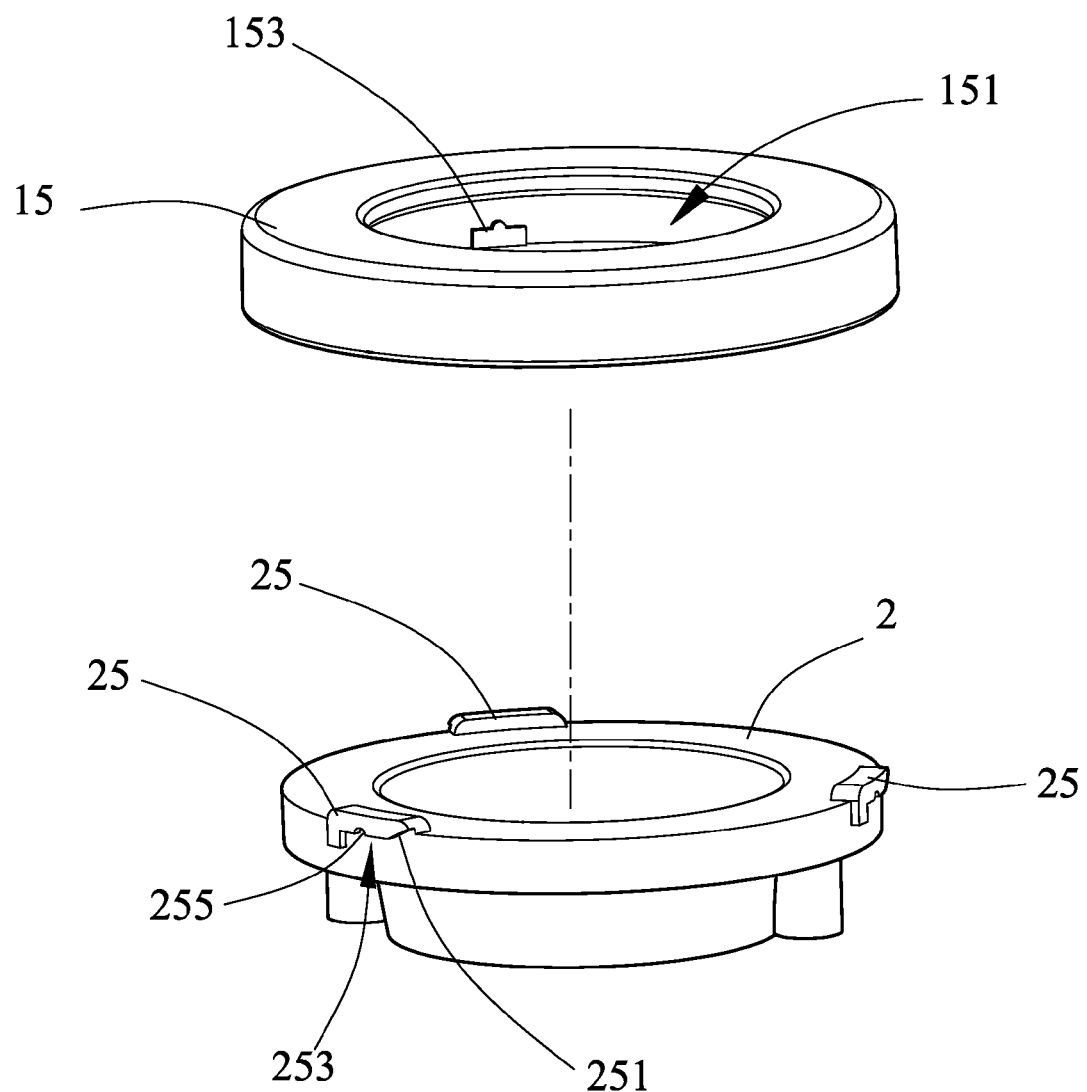
FIG. 6 is an assembled view of a cover and a heat-transfer container of the angle-adjustable aroma diffuser in accordance with the present invention.
Figure 7:
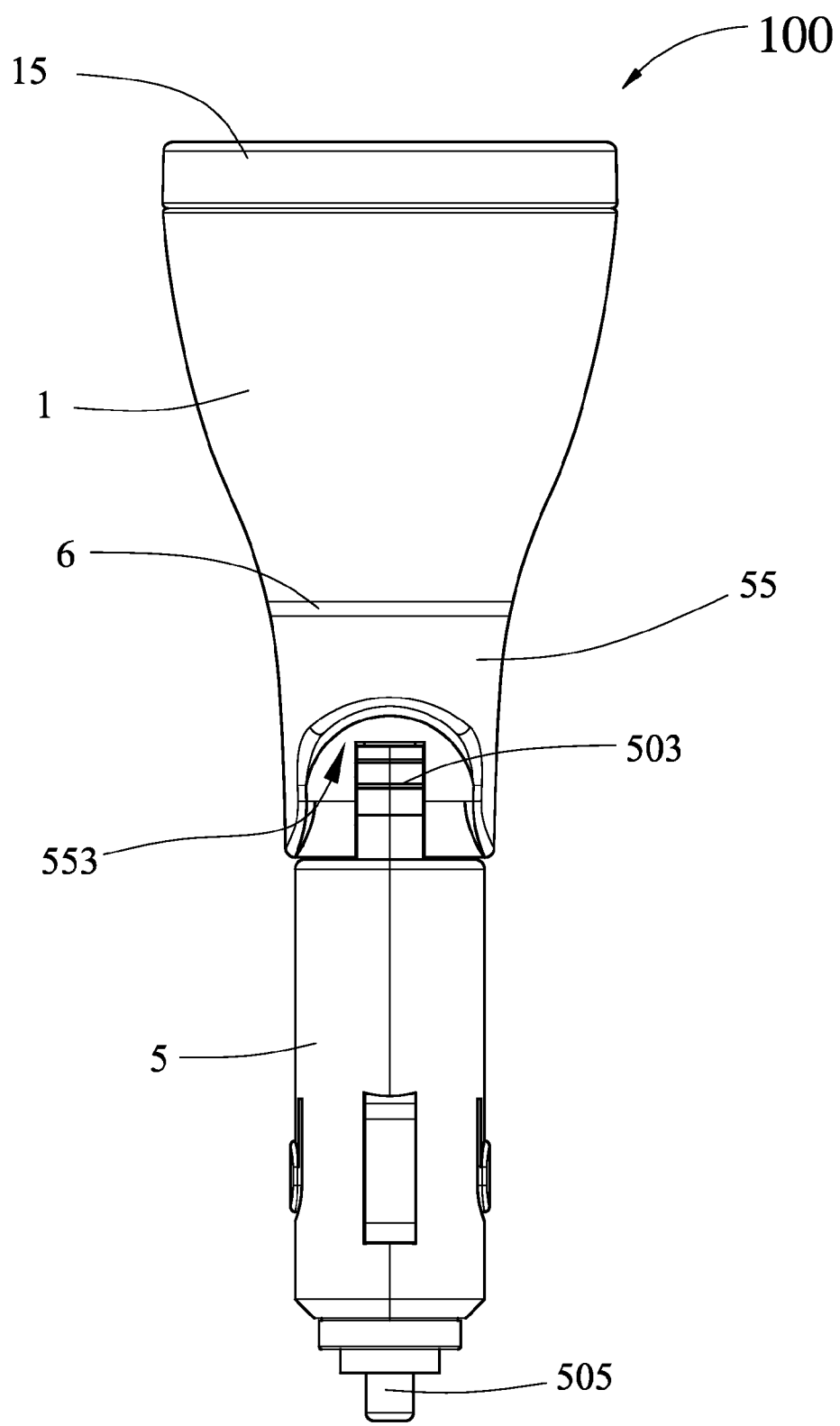
FIG. 7 is a rear view of the angle-adjustable aroma diffuser in accordance with the present invention.
Figure 9:
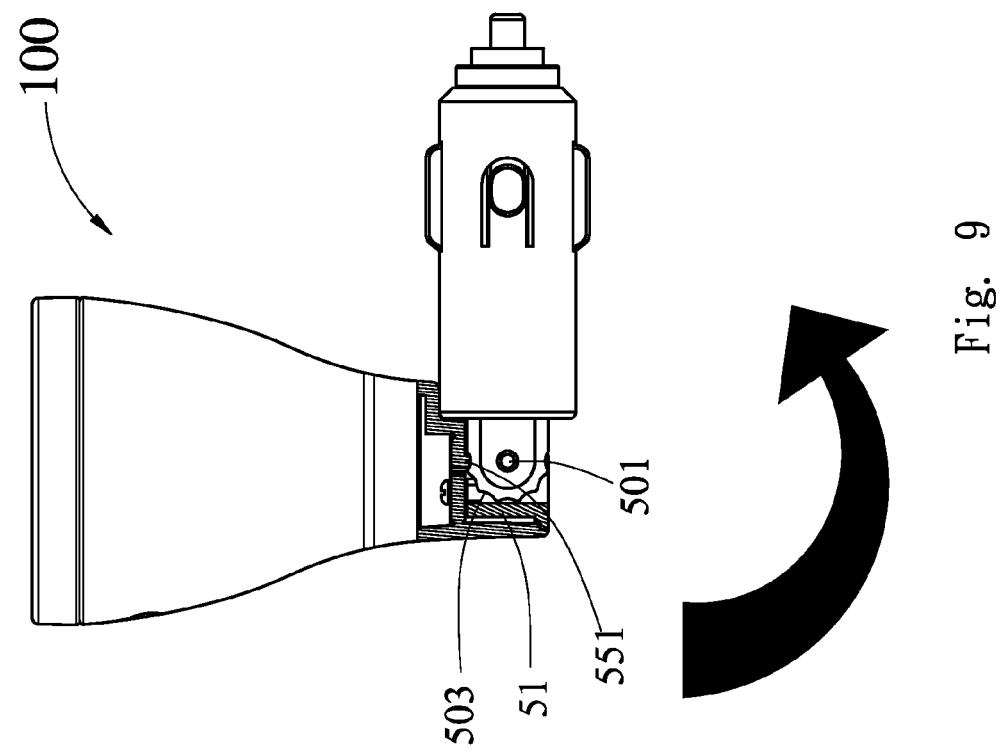
FIGS. 8 and 9 are cross-sectional views illustrating the operation of the angle-adjustable aroma diffuser in accordance with the present invention.
Figure 8:
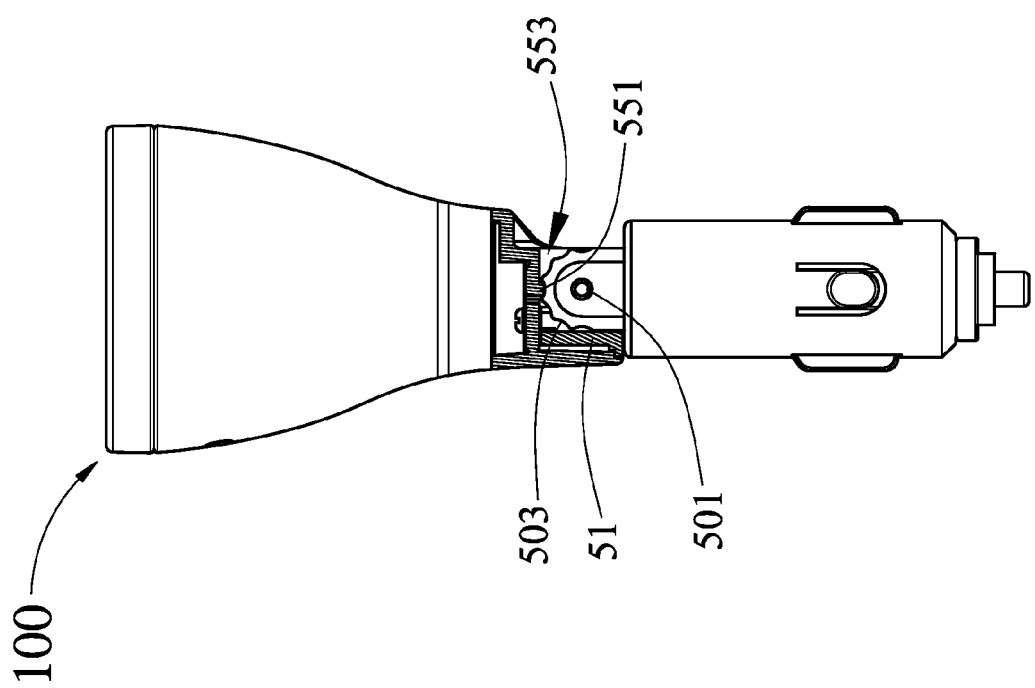

Please refer to FIG. 6. The heat-transfer container 2 further comprises a magazine 25 on an upper periphery thereof. The magazine 25 comprises a slope portion 251 and a groove portion 253 extending from the slope portion 251. The groove portion 253 has a concave portion 255 on a top side thereof. The angle-adjustable aroma diffuser 100 further comprises a cover 15. The cover 15 comprises a through hole 151 and a protrusion 153. The cover 15 is hooked to the concave portion 255 of the magazine 25 of the heat-transfer container 2 by using the protrusion 153.

Refer to FIGS. 2, 4, 5 and 10. The angle-adjustable aroma diffuser 100 is further mounted to an aroma capsule 7. The aroma capsule 7 is disposed in the heat-transfer container 2. The aroma capsule 7 further comprises a disposable capsule body 71 and an aromatic substance 75. The disposable capsule body 71 has a top opening 711. The aromatic substance 75 is disposed in the disposable capsule body 71. The aromatic substance 75 is an aromatic substance block, for example. The aromatic substance block is a solid aromatic wax and essential oil, for example. In an embodiment, the aromatic substance block is an aromatic wax. Therefore, the heating component 3, when being electrically connected to a power supply, will generate heat to the heat-transfer container 2. The heat-transfer plate 23 transfers the heat to the disposable capsule body 71 and the aromatic substance 75, for the aromatic substance 75 to generate fragrance.

Figure 4:
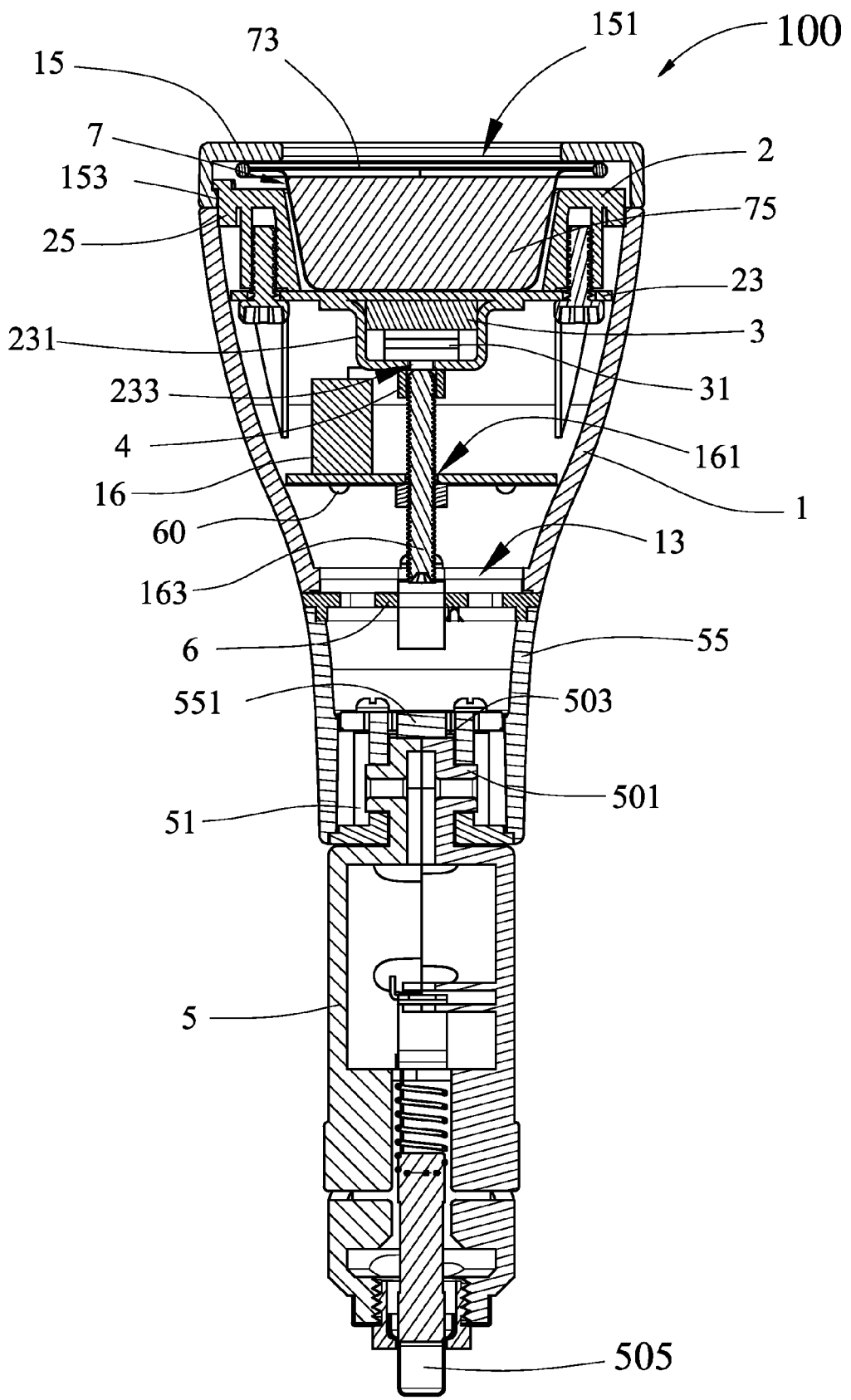
FIG. 4 is a cross-sectional view of the angle-adjustable aroma diffuser shown in FIG. 3 along a cutting line AA in accordance with the present invention.
Figure 5:
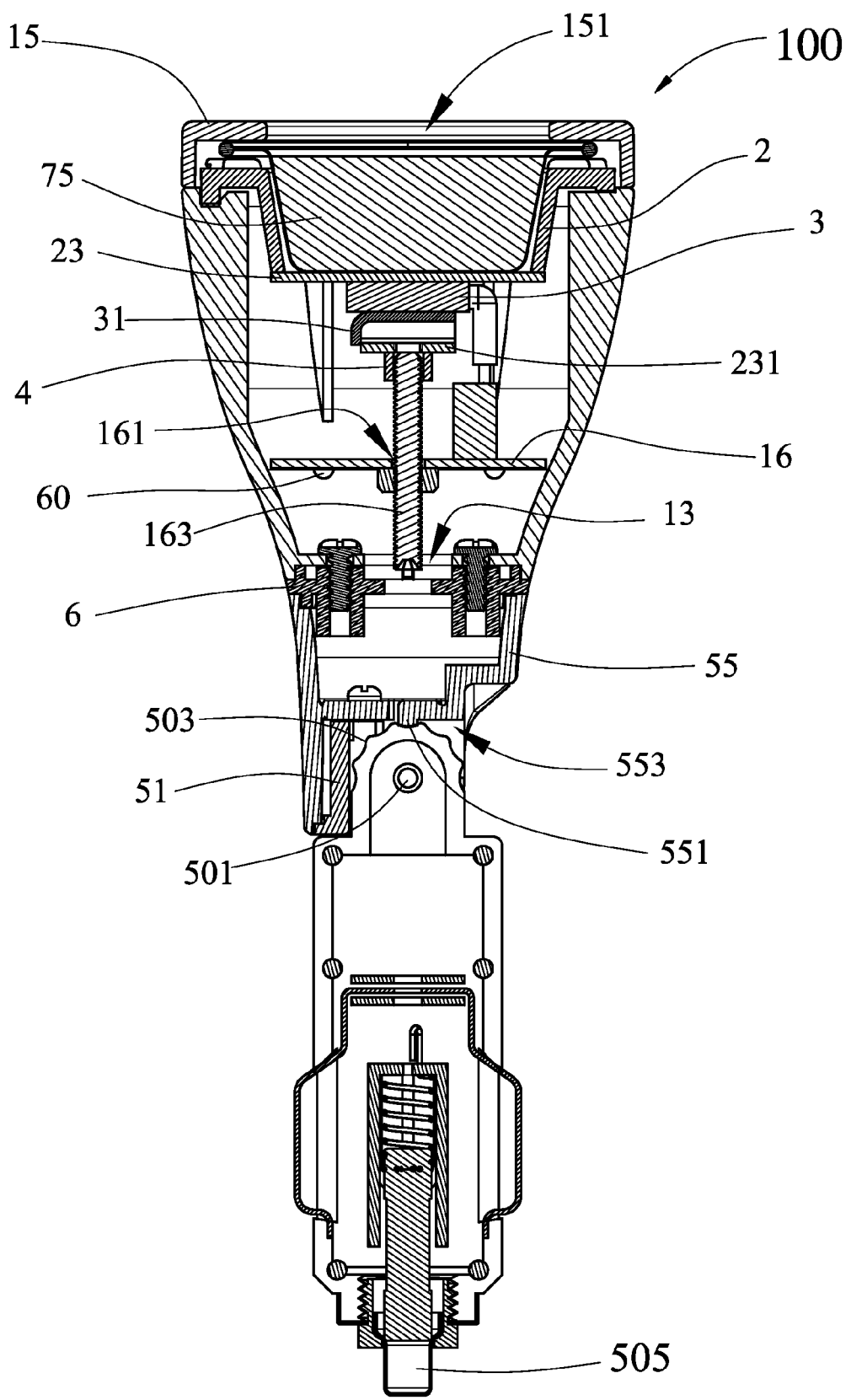
FIG. 5 is a cross-sectional view of the angle-adjustable aroma diffuser shown in FIG. 3 along a cutting line BB in accordance with the present invention.
Figure 10:
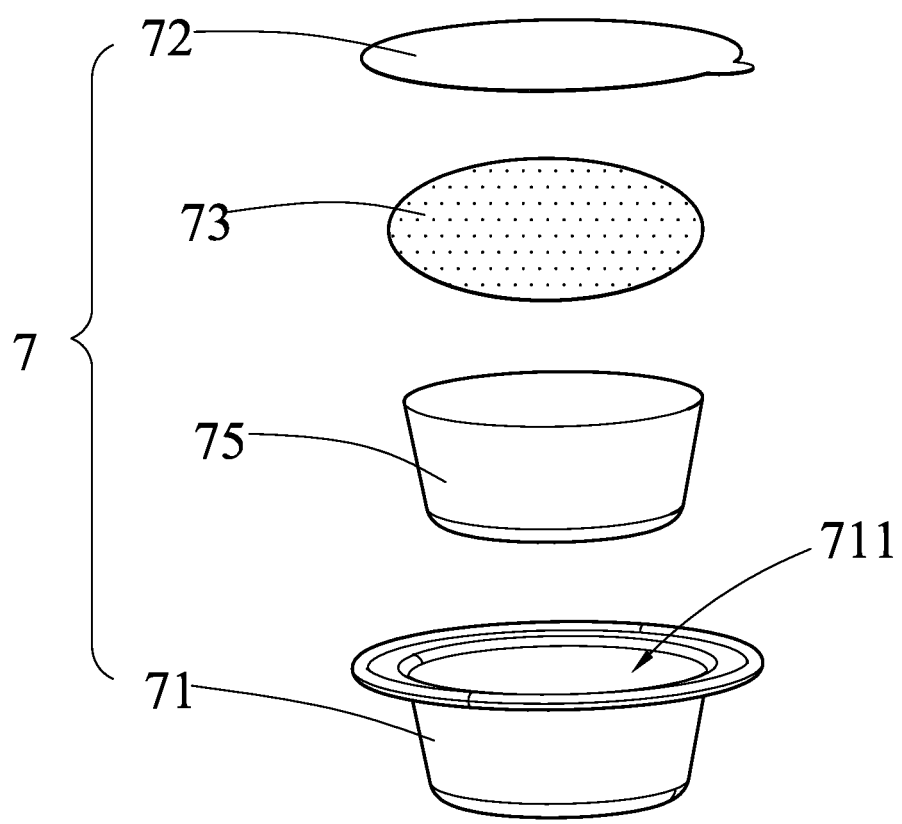
FIG. 10 is an exploded view of an aroma capsule of the angle-adjustable aroma diffuser in accordance with the present invention.

Please refer to FIGS. 4 and 10. The aroma capsule 7 further comprises a breathing film 73. The breathing film 73 is mounted to the top opening 711 of the disposable capsule body 71.

The breathing film 73 has an air vent that diffuses the fragrance of the aromatic substance 75 upward to an ambient environment. The breathing film 73 is a cloth (e.g., non-woven fabric, fiber cloth, linen, and canvas), fiber sheet, perforation film or perforation metal foil. In an embodiment, the breathing film 73 is made of a perforation film. The perforation film has its periphery mounted to the top opening 711 of the disposable capsule body 71. When angle-adjustable aroma diffuser 100 is toppled and fell accidentally, the aroma wax disposed in the disposable capsule body 71 will be blocked by the breathing film 73 from flowing in a car or another usage space. Therefore, the inner space of the car will not be contaminated, and the angle-adjustable aroma diffuser 100 is safe to use.

In an embodiment in accordance with the present invention in which the aroma capsule 7 is not mounted with the breathing film 73 or is mounted with the breathing film 73, the aroma capsule 7 further comprises a sealing cover 72 that is mounted to the top opening 711 of the disposable capsule body 71, for protecting the aromatic substance 75 (e.g., aroma wax) disposed in the aroma capsule 7 from being contaminated or losing its fragrance. In use, the sealing cover 72 is lifted up, and the aroma capsule 7 can be disposed in the heat-transfer container 2.

The disposable capsule body 71 is made of metal, hard plastic, fiber bowl (plant fibers, such as corn fiber, glass fiber and carbon fiber), or composition material.

In an embodiment, the disposable capsule body 71 is an aluminum foil bowl made of an aluminum foil. Therefore, the disposable capsule body 71 is thin and light, and has a well enough heat-transfer function. The disposable capsule body 71 can conduct the heat generated by the heating component 3 to the disposable capsule body 71 and the aromatic substance 75 such that the aromatic substance 75 is heated up and diffuses fragrance. The disposable capsule body 71 made of the aluminum foil is tough and is not likely to be broken, and is thus different from the fragile product, such as ceramic and glass bowl, that is disposed in a conventional heating device for contain essential oil and aroma wax.

Since the aromatic substance 75 is disposed in the disposable capsule body 71, rather than disposed in the conventional container, a user, when using the aromatic substance 75, is allowed to tear off the sealing cover 73 (referring to FIGS. 2 and 3), without worrying about being contaminated by the aromatic substance 75. When the aromatic substance 75 is heated up and volatile completely through the open end 21 of the heat-transfer container 2, a user is allowed to remove the disposable capsule body 71 from the open end 21 of the heat-transfer container 2, and place in the heat-transfer container 2 a new aroma capsule 7 that contains aromatic substance of the same or different fragrance. Since the disposable capsule body 71 has a housing that is made of an aluminum foil, a user does not need to worry about breaking or having to wash the disposable capsule body 71. The user also needs not to prepare an additional container for the aromatic substance 75 to be contained therein.

In an embodiment in accordance with the present invention, the angle-adjustable electric plug 5 is a car plug that can be combined with the aromatic substance that is used in a car. Therefore, a user is allowed to carry the aromatic substance in any car, and the aromatic substance will generate fragrance in the car.

It will be apparent to those skilled in the art that various modifications and variations can be made to the disclosed embodiments. It is intended that the specification and examples be considered as exemplary only, with a true scope of the invention being indicated by the following claims and their equivalents.

What is claimed is:

1. An angle-adjustable aroma diffuser, comprising:
   a hollow housing;
   a heat-transfer container;
   a heating component;
   an angle-adjustable electric plug;
   the hollow housing comprising a first opening and a second opening;
   the heat-transfer container being mounted in the hollow housing;
   the heat-transfer container having an open end facing toward the same direction as the first opening;
   the heating component being combined to a bottom side of the heat-transfer container;
   the angle-adjustable electric plug having one side combined with the second opening of the hollow housing;
   the angle-adjustable electric plug being electrically connected to the heating component;
   the heat-transfer container comprising a magazine disposed on a top periphery;
   the magazine comprising a slope portion and a groove portion extending from the slope portion;
   the groove portion having a concave portion disposed on a top side; and
   the angle-adjustable aroma diffuser comprising a cover having a through hole and a protrusion, and the cover is hooked in the concave portion of the magazine of the heat-transfer container by using the protrusion.

2. The angle-adjustable aroma diffuser of claim 1, wherein the angle-adjustable electric plug further comprises a pivot cover and a hollow pivot body,
   wherein the angle-adjustable electric plug comprises an axle, a ratchet disposed on one side of the axle, and an electric outlet disposed on the other side of the axle, the axle is disposed on an inner side of the ratchet, the pivot cover comprises an axle groove, the hollow pivot body comprises a damping block and a magazine, the damping block is formed on an inner side of the hollow pivot body, the magazine is disposed on one side of the hollow pivot body, the pivot cover is combined with one side of the hollow pivot body, the axle of the angle-adjustable electric plug passes through the axle groove, the ratchet props against the damping block, the angle-adjustable electric plug changes an angle through the axle in the magazine, the electric outlet is combined with a socket, the hollow housing of the angle-adjustable aroma diffuser and the heat-transfer container modulate an angle upward with respect to the angle-adjustable electric plug through the use of the ratchet and a damping function of the damping block.

3. The angle-adjustable aroma diffuser of claim 2, wherein the aroma diffuser further comprises a light-guiding ring and a light-emitting device, the light-emitting device is disposed in the aroma diffuser near one side of the light-guiding ring, and the light-emitting device is electrically connected to the electric outlet.

4. The angle-adjustable aroma diffuser of claim 1, wherein the heat-transfer container comprises a heat-transfer plate on a bottom portion thereof, and the heat-transfer plate is combined with or formed on a bottom side of the heat-transfer container.

5. The angle-adjustable aroma diffuser of claim 4, wherein the heat-transfer container further comprises a screw bracket disposed on the bottom side of the heat-transfer plate and a screw, the screw bracket comprises a screw hole, the heating component props against a bottom portion of the heat-transfer plate, the heating component has a bottom side combined with a cushion pad, the heating component and the cushion pad are disposed on an inner side of the screw bracket, the screw passes through the screw hole and props against the cushion pad to push the heating component upward such that the heating component is in close contact with the heat-transfer plate disposed on a bottom portion of the heat-transfer container.

6. The angle-adjustable aroma diffuser of claim 5, wherein the heat-transfer container is an insulating material, the heat-transfer plate is metal, and the heating component generates heat that is transferred to the heat-transfer plate to heat the aroma capsule, without diffused to a region outside of the hollow housing.

7. The angle-adjustable aroma diffuser of claim 5, wherein the angle-adjustable aroma diffuser further comprises a PCB disposed in the hollow housing, the PCB is electrically connected to the angle-adjustable electric plug and the heating component, the PCB comprises another screw hole, the another screw has one end passing through the screw hole, the another screw has one end screwed to the hollow housing and the other end combined with the screw bracket, a heat-proof hollow pillar is combined with one end of the another screw and in contact with the screw bracket on the bottom side of the heat-transfer plate, for isolating the heat generated by the heating component from being transferred to the PCB.

8. The angle-adjustable aroma diffuser of claim 5, wherein the cushion pad is L-shaped, and the L-shaped cushion pad props against the heating component in the screw bracket.

9. The angle-adjustable aroma diffuser of claim 1, further comprising an aroma capsule disposed in the heat-transfer container, wherein the aroma capsule further comprises a disposable capsule body and an aromatic substance, the disposable capsule body has a top opening, the aromatic substance is disposed in the disposable capsule body, and the aroma capsule further comprises a breathing film that is combined with the top opening of the disposable capsule body.

* * * * *